United States Patent [19]

Ross

[11] Patent Number: Plant 7,142

[45] Date of Patent: Feb. 6, 1990

[54] MALUS CORAL CASCADE

[76] Inventor: Henry A. Ross, 16711 Pearl Rd., Strongsville, Ohio 44136

[21] Appl. No.: 292,113

[22] Filed: Dec. 30, 1988

[51] Int. Cl.[4] ..... A01H 5/00

[52] U.S. Cl. ..... Plt./34

[58] Field of Search ..... Plt./34

[56] References Cited

U.S. PATENT DOCUMENTS

P.P. 4,038 4/1977 Zampini ..... Plt. 34

*Primary Examiner*—James R. Feyrer

[57] ABSTRACT

Named for its graceful, semi-weeping habit and persistant coral-orange fruit, Malus cultivar 'Coral Cascade' offers a unique fall display among crabapple cultivars with a weeping habit. The abundant load of large pea-sized ornamental fruit causes its slender horizontal branches to droop in a cascade of reddish-orange color. Its annual fruit production results in a permanent downward arching of the branches as the plant ages. This crabapples small stature (15′ tall×20′ wide in 30 years) makes it desirable for use in prominant landscape locations, elevated planters, and beneath power lines. The spring flower display starts with pinkish-red buds on pendulous pedicels of about 1.5″ (4 cm) in length. The abundant flowers open white with the abaxial edges of the petals remaining pink. 'Coral Cascade' has an established record of disease resistance. Its thick, green leaves retain their high quality until fall frosts transform them to golden hues of yellow, orange and tan.

2 Drawing Sheets

BACKGROUND OF THE NEW VARIETY

The present invention relates to a new and distinct variety of Malus tree, created by me; a Clonal selection designated as Malus 'Coral Cascade'. Although its parentage is unknown, it is of Malus×Zumi ancestry (*Malus baccata mandshurica*×*Malus Sieboldi*). This new clone of Malus has been selected on the basis of the following characteristics 1. Its graceful spreading-cascading habit of growth, especially when loaded with fruit in the Fall.
2. Its profuse and striking annual display of an unusual and uncommon coral-orange fruit.
3. Its high resistance to diseases which often affect Malus.

In 1950, when varieties of ornamental flowering crabapples, available commercially, were very limited; I embarked upon a program intended to produce superior new clones with various superior characteristics pertaining to flowers, fruit, size, habit of growth, disease resistance, annual blooming, etc. I began by obtaining almost all of the varieties then available commercially, as well as propagating varieties not commercially available by obtaining scions from various botanical gardens, and grafting them onto apple seedlings. As these developed, I began collecting open-pollinated seed from those which appeared promising and starting hundreds of thousands of seedlings, from which I always selected . . . at the earliest stage . . . those which appeared different, and discarded the rest. As the selected seedlings developed, I collected open-pollinated seed from those which appeared promising and, from the resulting seedlings, continued to keep only those which appeared different, and discarded the rest. Out of the countless thousands of seedlings started, I eventually had planted out, for further evaluation, approximately 500 selections which showed promise for one reason or another. Out of these selections, two were patented in the early 1970's and others appear to be worthy of patenting. About 1958 a seedling selection was observed which had a very uncommon cascading habit of growth and produced, each year, an enormous and very striking display of small, glossy fruit of a distinctive and uncommon coral-orange color; and appeared free from all Malus diseases. This selection was always greatly admired by visitors and eventually became so distinctive that it was given the name of 'Coral Cascade' and was selected to be patented and introduced upon the issuance of a patent.

Over the years, I have vegetatively propagated Malus 'Coral Cascade', by grafting scions of it onto seedlings of apple or crabapple and the resulting progeny have all proven to be identical, in all respects, with the original tree.

BRIEF DESCRIPTION OF THE PHOTOGRAPHS ATTACHED

The first sheet contains 2 photographs taken at the Gardenview Horticultural Park at Strongsville, Ohio, (where the tree originated), during the Fall of 1988 and are of the original tree now approximately 30 years old and presently approximately 14 feet tall and 20 feet wide. The upper photograph shows a portion of this original tree in fruit. The lower photograph shows a portion of this tree in fruit, illustrating the cascading habit of growth and the profuse display of fruit of an uncommon coral-orange color.

The second page contains 3 photographs of a vegetatively propagated offspring of the original tree. The top photograph shows a single plant approximately 6½ feet tall, in fruit. The middle photograph shows the flowers of this plant taken in the Spring and the bottom photograph shows a fruiting portion of this plant exhibiting the cascading habit of growth and heavy display of coral-orange fruit.

BOTANICAL DESCRIPTION

A. 'Coral Cascade' is a Malus seedling selected from an open pollinated seed source of *Malus*×*zumi* var. calocarpa. Its flowering period coincides with *Malus*×*zumi* var. calocarpa and most other crabapple cultivars. It blooms after the early crabapples and well before the late (native) crabs.

B. Flowers

The flowers of this tree are single. The color at the tight bud stage is pinkish-red (Fan 1 Red Group 54A) (RHS Colour Chart Fans, issued by the Royal Horticultural Society of London, England; in association with the Flower Council of Holland). At the balloon stage the color lightens to pink. The petals open white, while retaining a band of pink on the exterior edge (Fan 1 Red Group 55A or 55B) Pedicels vary in length from 1–2¼" (25–55 mm) with a 1½" (38.7 mm) average. Flowers are borne in umbels and vary in number from 2–7 per spur. The average number of flowers per spur is 4.5; usually there are 4 or 5 flowers per spur. Flowering on interior spurs is abundant, but number per spur is reduced. The flower size ranges from 1–1½" (25–38 mm). 'Coral Cascade' consistantly produces a profuse flower display on an annual basis.

C. Habit

The habit of this crabapple is one of its most distinctive features, making it unique even among the weeping crabapples. Lateral scaffold branches emerge irregularly at wide angles of 45 to 90. Young trees tend to show nearly horizontal scaffold branches of medium texture. In mature trees, the branches are gracefully arched in a compact form that renders plants of this cultivar so distinctive. Branchlets emanate irregularly from the scaffold branches and tend to bend downward once they bear fruit. The thin, wiry nature of the branches and twigs and the persistance of the abundant fruit produce the semi-cascade form that gives this tree its unique shape.

D. Bark

The small branchlets are chestnut red. Lenticels are tan when young, gray when older, slightly raised, and not particularly prominant. 1/16" (1.5 mm) or less broad and less than 1/32" (1 mm) long. The bark of the branches is smooth, ochre or butterscotch and partially covered with waxy bloom.

E. Fruit

Fruits vary from ¼" to ⅝" (7 to 15 mm) and average ½" (12 mm) in diameter. They mature glossy, reddish-orange (coral orange closest to RHS Fan 1 Orange Red Group 35A-35B) and are subspherical to obovoid. Lenticel dots are inconspicuous and scattered. The calyx is not persistant. The calyx scar is tan, slightly crateriform, with a slightly raised circular apex. Fruit flesh is yellow. There are 3 or 4 carpels per fruit, each with 1 or 2 seeds. Seeds are ⅛–5/32" (3–4 mm) long and 5/64–⅛" (2–3 mm) wide with a smooth brown seed coat typical of Malus. Fruits are persistant until hard frost when they soften and are eaten by birds.

F. Leaves

Leaves are narrowly to broadly elliptic. Blades are 2¾–3⅛" (7–8 cm) long and 1 9/16–1¾ (4–4.5 cm) wide. The blades tend to curl upwardly and inwardly exposing the abaxial leaf surface and midrib. Leaf bases are obtuse to cuneate, not uncommonly somewhat oblique. Leaf apices are abruptly acuminate, occasionally acute. Margin are serrate, sometimes doubly-serrate distally. Leaves on vigorous shoots are occasionally lobed. Petioles are often narrowly winged distally, and maroon in color, especially abaxially, and tomentulose. This pigmentation extends into at least the basal portion of the abaxial leaf midvein. Stipules are serrate. Leaves are subcoriaceous, glabrous above, except tomentulose along the proximal midvein, glabrate to sparsely tomentose below, especially along the midvein.

G. Disease resistance

Professor Les Nchols did not detect any apple scab, fire blight, cedar-apple rust, powdery mildew, or frog-eye leaf spot when evaluated from 1972 through 1978. The clean foliage late in summer indicates freedom of mite injury common to many crabapples. The fruit shows no evidence of insect infestation. No other major insect pest has been noted on any of the trees evaluated.

I claim:

1. A new and distinctive variety of flowering crabapple tree, as described and illustrated, a clone which is especially distinctive because of its wide-spreading, cascading habit of growth, especially when loaded with fruit in the Fall; an extremely profuse and striking annual display of persistant, small, glossy fruit of an unusual and uncommon coral-orange coloration; as well as being easily propagated vegetatively and coming true to the original selection, fairly rapid growing and apparently free from diseases which normally affect flowering crabapples.

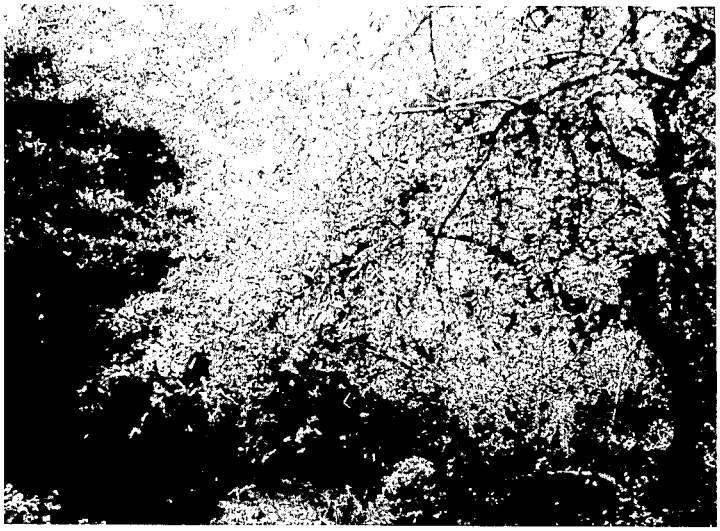
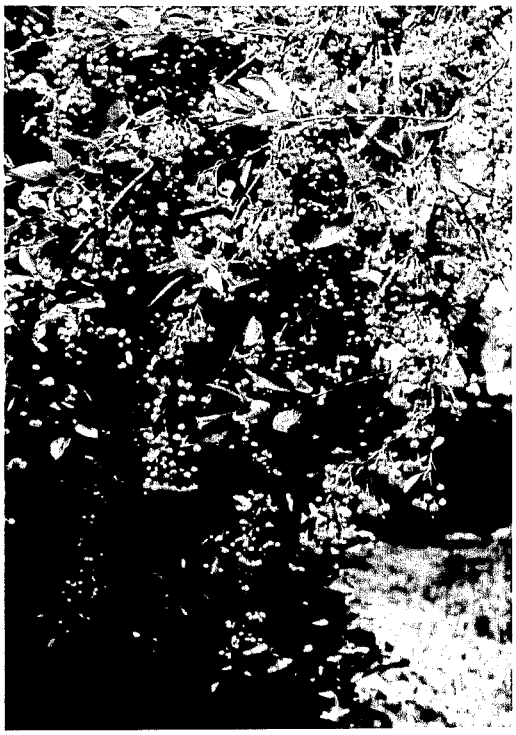

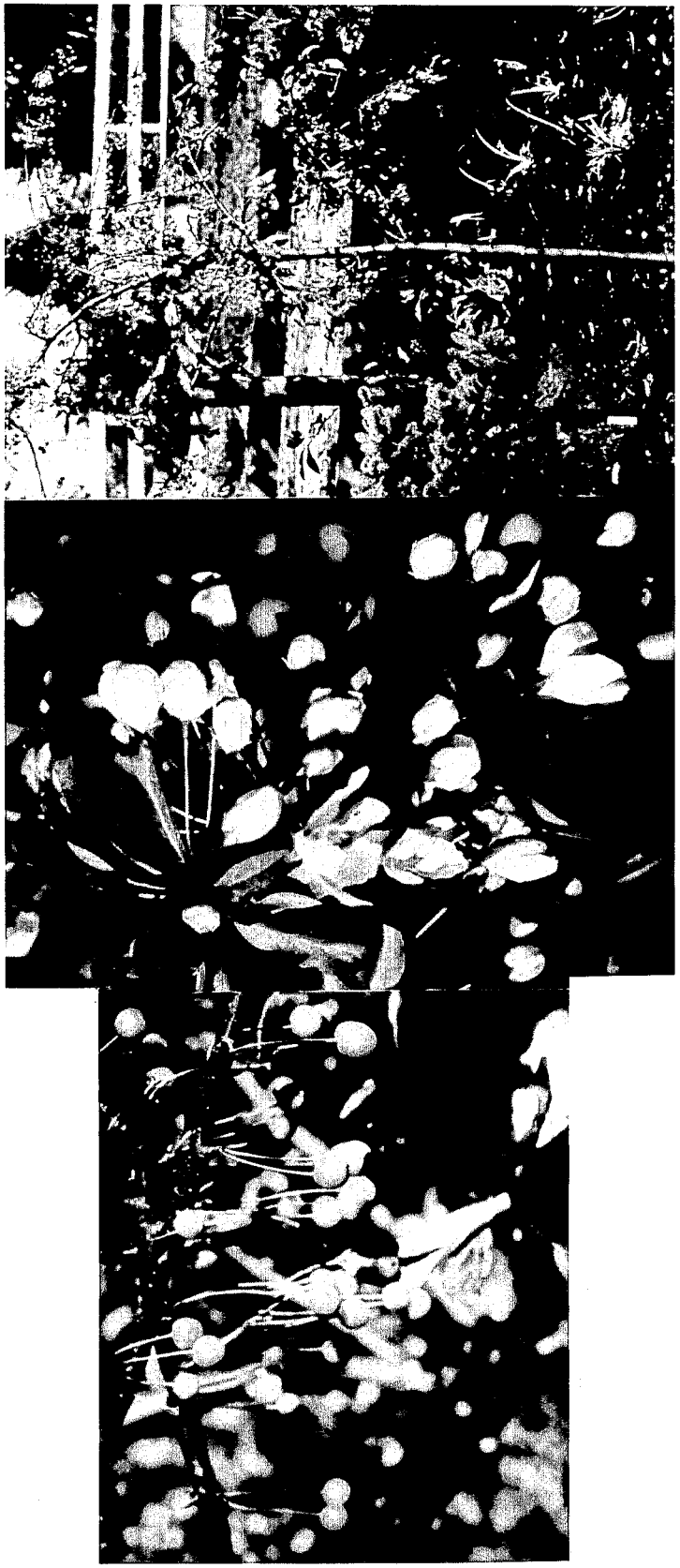

* * * * *